United States Patent
Chen (10) Patent No.: US 9,044,295 B2
(45) Date of Patent: Jun. 2, 2015

(54) INTERDENTAL CLEANING DEVICE

(71) Applicant: Geefloss Corporation, New Taipei (TW)

(72) Inventor: Ming-Hsiang Chen, New Taipei (TW)

(73) Assignee: Geefloss Corporation, New Taipei (TW)

( * ) Notice: Subject to any disclaimer, the term of this patent is extended or adjusted under 35 U.S.C. 154(b) by 0 days.

(21) Appl. No.: 14/156,125

(22) Filed: Jan. 15, 2014

(65) Prior Publication Data

US 2014/0196743 A1    Jul. 17, 2014

(30) Foreign Application Priority Data

Jan. 17, 2013   (TW) .................................. 102101804

(51) Int. Cl.
*A61C 15/00*    (2006.01)
*A61C 15/04*    (2006.01)

(52) U.S. Cl.
CPC ..................... *A61C 15/046* (2013.01)

(58) Field of Classification Search
USPC .................................................. 132/323–328
See application file for complete search history.

(56) References Cited

U.S. PATENT DOCUMENTS

| | | | | |
|---|---|---|---|---|
| 553,610 A | * | 1/1896 | Falkensteitn | 132/325 |
| 1,180,620 A | * | 4/1916 | Stuart | 132/324 |
| 5,482,466 A | * | 1/1996 | Haynes | 132/323 |
| 5,881,744 A | * | 3/1999 | Lo | 132/325 |
| 2006/0266378 A1 | * | 11/2006 | Liu et al. | 132/325 |

FOREIGN PATENT DOCUMENTS

| | | |
|---|---|---|
| JP | 2-12975 Y2 | 4/1990 |
| JP | 1990-12975 | 4/1990 |
| TW | M280785 U | 11/2005 |
| TW | M289638 U | 4/2006 |

OTHER PUBLICATIONS

Extended European Search Report dated Apr. 23, 2014, issued by the European Patent Office in corresponding European Patent Application No. 14151315.0 (6 pages).
Search Report appended in an Office Action issued by the Taiwan Intellectual Property Office on Jul. 21, 2014, in corresponding Taiwan Patent Application No. 102101804, with an English translation thereof (2 pages).

* cited by examiner

*Primary Examiner* — Rachel Steitz
(74) *Attorney, Agent, or Firm* — Osha Liang LLP (57) ABSTRACT

An interdental cleaning device is adapted for use with a dental floss roll and includes a main body and a floss holder. The main body defines a receiving space configured to receive the dental floss roll. The floss holder is pivotally connected to the main body and defines a guiding channel that is in spatial communication with the receiving space. The floss holder has a securing end, and an open end that is spaced apart from the securing end and that is formed with an opening to spatially communicate the guiding channel with external environment. A to-be-used segment of the dental floss roll is extendible through the opening of the open end via the guiding channel so as to be secured at the securing end of the floss holder.

12 Claims, 14 Drawing Sheets

INTERDENTAL CLEANING DEVICE

CROSS-REFERENCE TO RELATED APPLICATION

This application claims priority of Taiwanese Application No. 102101804, filed on Jan. 17, 2013.

BACKGROUND OF THE INVENTION

1. Field of the Invention

The invention relates to a cleaning device, more particularly to an interdental cleaning device.

2. Description of the Related Art

European Patent Application Publication No. 0339935 B1 discloses an F-shape conventional interdental cleaning device including a rod-like handle portion, two rod-like spaced-apart protruding portions protruding from the handle portion, and a dental floss stretched tautly between the protruding portions. When using the conventional interdental cleaning device, the dental floss needs to be placed into one of interdental spaces. However, since interdental spaces extend in various directions (e.g., the interdental space between incisors extends in a direction different from that between molars), it is inconvenient to use the conventional interdental cleaning device to clean the interdental space between the molars.

SUMMARY OF THE INVENTION

Therefore, the object of the present invention is to provide an interdental cleaning device that may alleviate the aforementioned drawback of the prior art.

Accordingly, an interdental cleaning device of the present invention is adapted for use with a dental floss roll and comprises a main body and a floss holder.

The main body defines a receiving space configured to receive the dental floss roll.

The floss holder is pivotally connected to the main body and defines a guiding channel that is in spatial communication with the receiving space. The floss holder has a securing end and an open end that is spaced apart from the securing end and that is formed with an opening to spatially communicate the guiding channel with external environment.

A to-be-used segment of the dental floss roll is extendible through the opening of the open end via the guiding channel so as to be secured at the securing end of the floss holder.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail, it should be noted that like elements are denoted by the same reference numerals throughout the disclosure.

Figure 1:
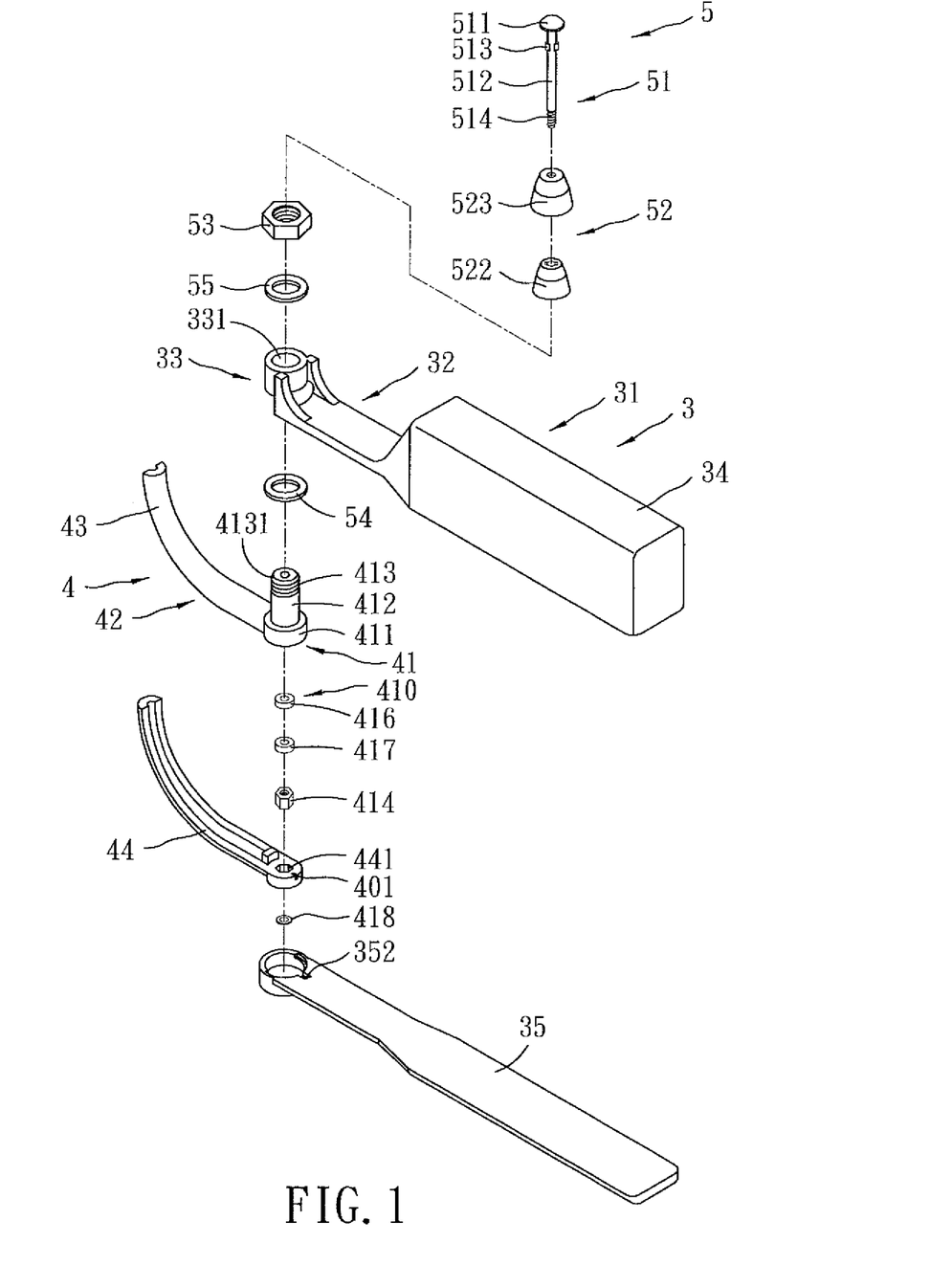
FIG. 1 is an exploded perspective view of a first preferred embodiment of an interdental cleaning device according to the invention.
Figure 2:
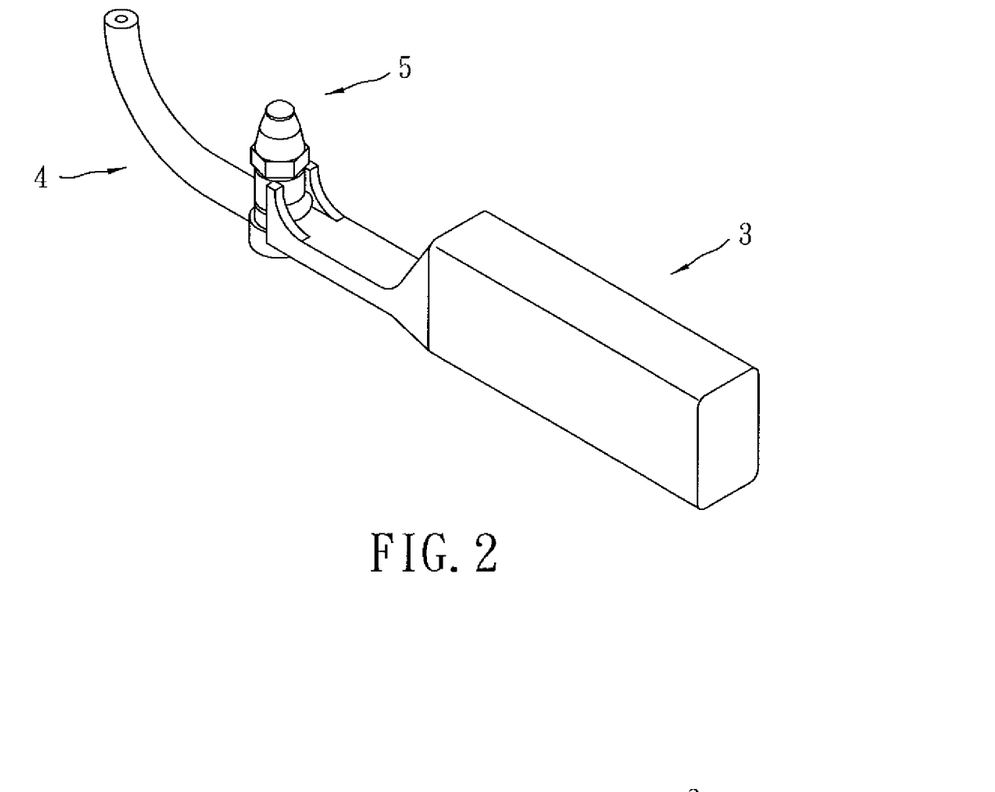
FIG. 2 is a perspective view of the first preferred embodiment.
Figure 3:
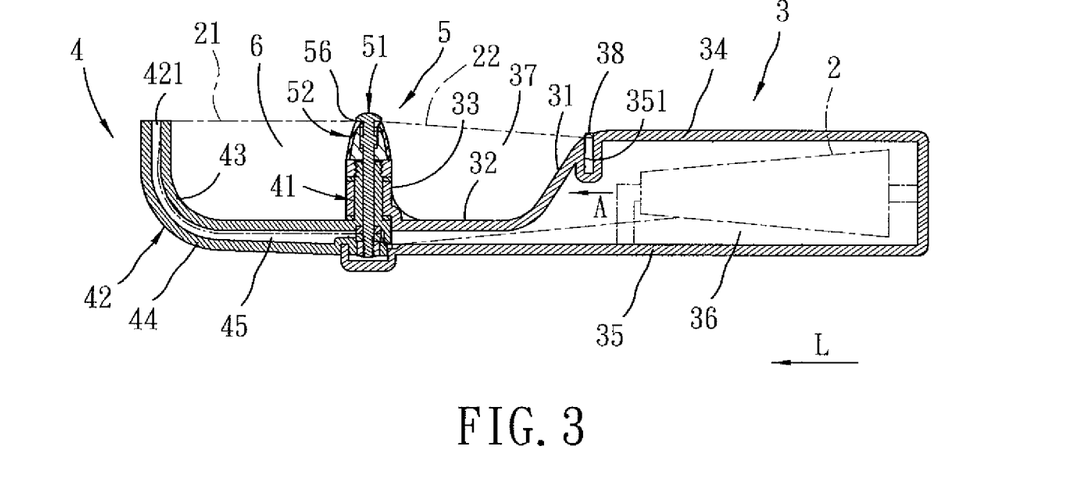
FIG. 3 is a sectional view of the first preferred embodiment.

Referring to FIGS. 1 to 3, the first preferred embodiment of an interdental cleaning device according to the present invention is adapted for use with a dental floss roll 2 to clean an interdental space 1 (see FIG. 9), and includes a main body 3 and a floss holder 4.

The main body 3 has a handle portion 31, an extending portion 32, and a connecting portion 33. The extending portion 32 extends from one side of the handle portion 31 and has a height less than that of the handle portion 31. The connecting portion 33 is connected to the extending portion 32, is spaced apart from the handle portion 31, and is formed with a through hole 331. The main body 3 defines a receiving space 36 configured to receive the dental floss roll 2. In this embodiment, the main body 3 is formed by securing a first body piece 34 and a second body piece 35 to each other.

The floss holder 4 is pivotally connected to the main body 3 and includes a sleeve portion 41 extending into the through hole 331 of the connecting portion 33, and a bow portion 42 that extends from one side of the sleeve portion 41 and that is rotatable relative to the connecting portion 33 of the main body 3. In this embodiment, the floss holder 4 is formed by securing first and second holder pieces 43, 44 to each other. The holder pieces 43, 44 cooperatively define a guiding channel 45 therebetween.

The floss holder 4 further includes an adjusting unit 5 including an adjusting screw 51 that extends into and is retained at the sleeve portion 41, and an adjusting cap 52 that is sleeved on and is co-rotatably coupled to the adjusting screw 51. In this embodiment, as shown in FIG. 1 and further referring to FIG. 4, the adjusting cap 52 is formed with a through bore 524 and two opposite engaging trenches 525 extending radially outward from and in spatial communication with the through bore 524. The adjusting screw 51 has a head portion 511, a shank portion 512, and two linking portions 513. The head portion 511 is disposed to abut against the adjusting cap 52. The shank portion 512, which has a diameter less than that of the head portion 511, is connected to the head portion 511 and extends through the through bore 524 of the adjusting cap 52. Each of the linking portions 513 protrudes from an outer surface of the shank portion 512, which is proximate to the head portion 511, and engages a respective one of the engaging trenches 525 of the adjusting cap 52 thereby coupling co-rotatably the adjusting screw 51 and the adjusting cap 52. Although the adjusting cap 52 has two of the engaging trenches 525 and the adjusting screw 51 has two of the linking portions 513 in this embodiment, it should be noted that one linking portion 513 and one engaging trench 525 may suffice such that the number thereof should not be limited to the disclosure of this embodiment.

Figure 5A:
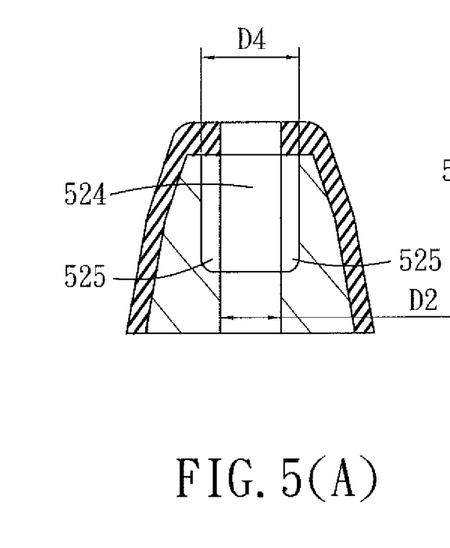
FIG. 5(A) is a sectional view of the first preferred embodiment to illustrate an adjusting screw.
Figure 5B:
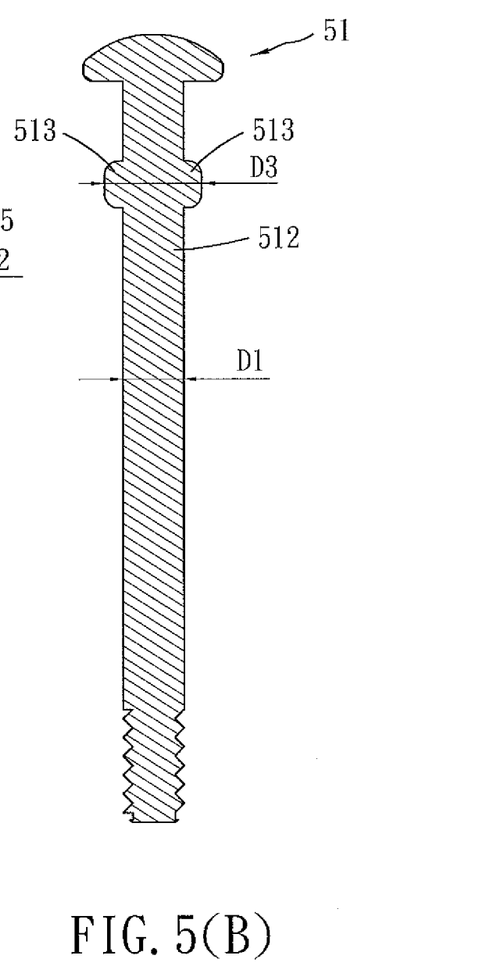
FIG. 5(B) is a sectional view of the first preferred embodiment to illustrate an adjusting cap.
Figure 6:
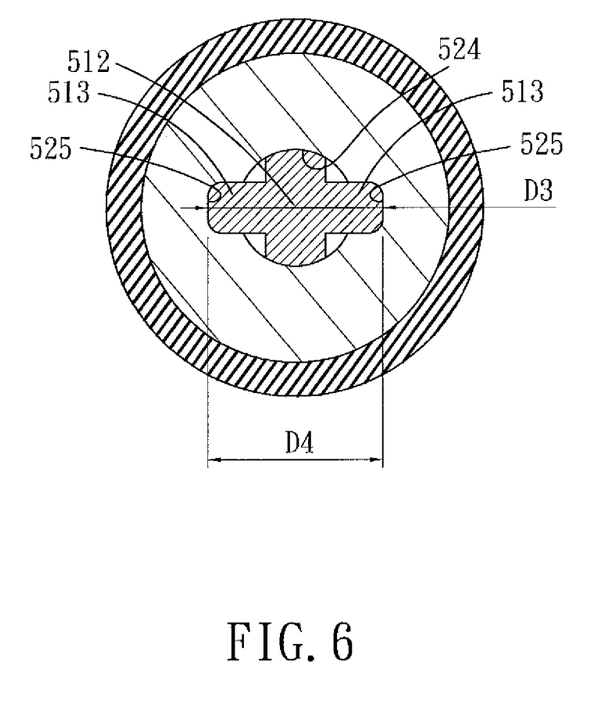
FIG. 6 is another sectional view of the first preferred embodiment, illustrating the adjusting screw and the adjusting cap.

In this embodiment, the adjusting cap 52 has a first surrounding portion 522 formed with the engaging trenches 525, and a second surrounding portion 523 disposed on the first surrounding portion 522. The second surrounding portion 523 has an abutting section 5231 that is disposed to abut against the head portion 511 of the adjusting screw 51, and a surrounding section 5232 that is connected to the abutting section 5231 and that cooperates with the abutting section 5231 to cover the first surrounding portion 522. The through bore 524 is formed through the first surrounding portion 522 and the second surrounding portion 523. Further referring to FIGS. 5(A), 5(B) and 6, an outer diameter D1 of the shank portion 512 of the adjusting screw 51 is slightly less than an inner diameter D2 of the through bore 524 of the adjusting cap 52 so that the shank portion 512 may be received in the through bore 524 (see FIGS. 5(A) and 5(B)). In addition, a segment of the adjusting screw 51, which is provided with the linking portions 513, has a non-circular cross-section corresponding to the cross-sectional shape formed by the engaging trenches 525 and the through bore 524, thereby coupling co-rotatably the adjusting screw 51 and the second surrounding portion 523 of the adjusting cap 52 (see FIG. 6). In this embodiment, the linking portions 513 are configured as ribs extending in an extending direction of the through bore 524, and each of the engaging trenches 525 is configured to accommodate the respective one of the linking portions 513 therein. Moreover, a distance D3 between lateral sides of the opposite linking portions 513 is slightly less than a distance D4 between innermost surfaces of the engaging trenches 525 so that the linking portions 513 may be received in the engaging trenches 525 to co-rotatably couple the adjusting screw 51 to the adjusting cap 52.

Referring once again to FIGS. 1, 3 and 4, in this embodiment, the sleeve portion 41 of the floss holder 4 has a base segment 411, a post segment 412, and an exposed segment 413. The post segment 412 extends from the base segment 411 into the through hole 331 of the connecting portion 33 and has a diameter less than that of the base segment 411. The exposed segment 413, which extends from the post segment 412, is exposed from the through hole 331 of the connecting portion 33 and is formed with an external screw thread 4131 (see FIGS. 1 and 3). The adjusting unit 5 further includes an adjusting nut 53, a first washer 54 and a second washer 55. The adjusting nut 53 is disposed between the connecting portion 33 and the adjusting cap 52 and engages the external screw thread 4131 on the exposed segment 413. The first washer 54 is sleeved on the post segment 412 and is disposed between the connecting portion 33 and the base segment 411. The second washer 55 is sleeved on the post segment 412 and is disposed between the adjusting nut 53 and the connecting portion 33.

In this embodiment, the shank portion 512 of the adjusting screw 51 has a distal end that is distal from the head portion 511 and that is formed with an external screw thread 514. The floss holder 4 further includes a screw nut 414 that is received in a nut-receiving hole 441, which is formed at the second holder piece 44, and that engages the external screw thread 514 of the adjusting screw 51, so as to retain the adjusting screw 51 at the sleeve portion 41 and to pivotally connect the sleeve portion 41 to the connecting portion 33 of the main body 3.

Figure 4:
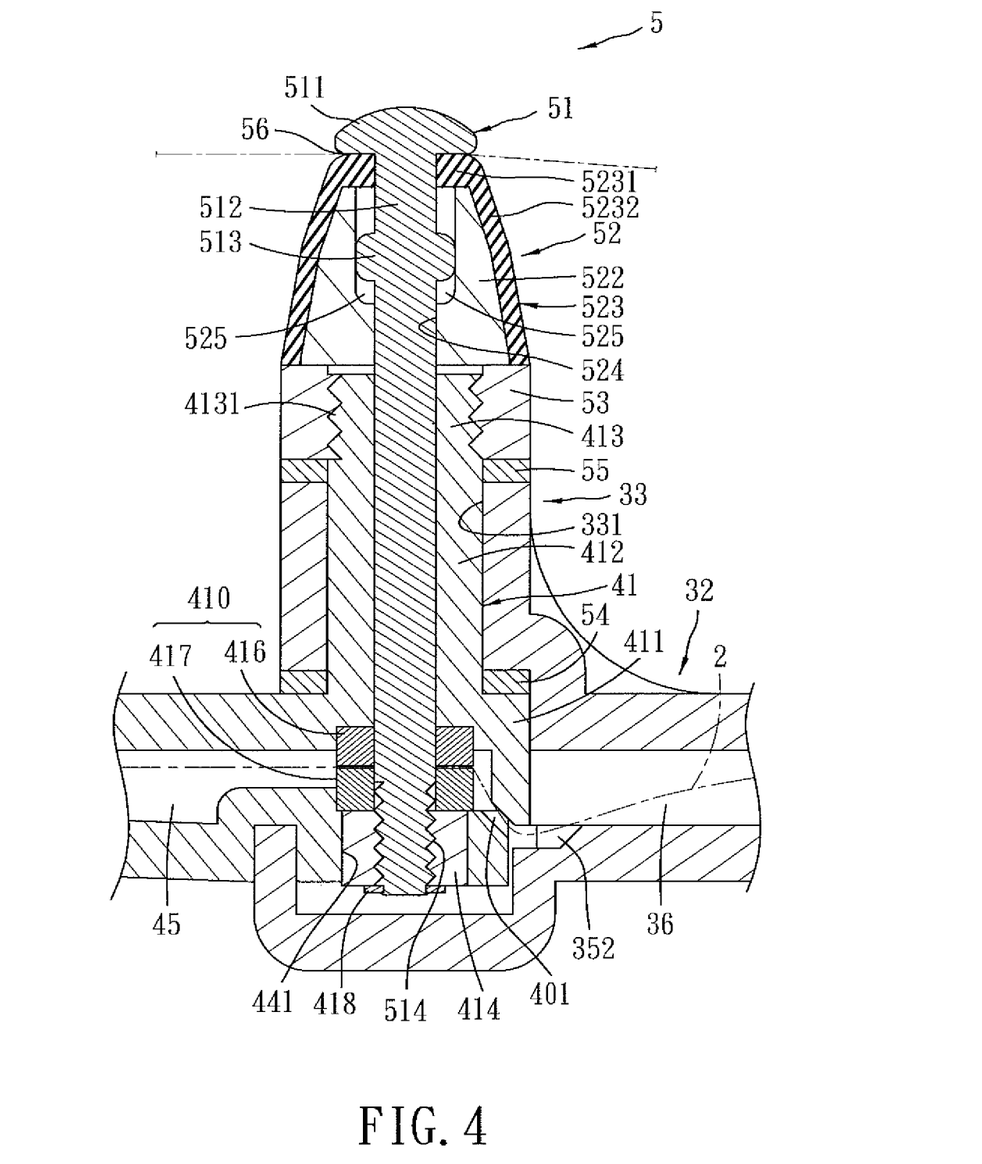
FIG. 4 is an enlarged fragmentary sectional view of the first preferred embodiment.

Preferably, as shown in FIGS. 1 and 4, the floss holder 4 further includes a screw washer 418 that is sleeved on the adjusting screw 51 and that is proximate to the screw nut 414. In this embodiment, the screw washer 418 is, but not limited to, a flat washer (e.g., the third washer may also be a plum washer).

As shown in FIGS. 1, 3 and 4, the main body 3 is configured substantially in a shape of a strip and defines a longitudinal direction (L). The second body piece 35 is formed with a dental floss outlet 352, and the second holder piece 44 is formed with a dental floss inlet 401 that spatially communicates with the dental floss outlet 352 so as to establish spatial communication between the receiving space 36 of the main body 3 and the guiding channel 45 of the floss holder 4. The dental floss roll 2 defines a roll axis (A). In this embodiment, the roll axis (A) of the dental floss roll 2 is parallel to the longitudinal direction (L) of the main body 3.

Figure 7:
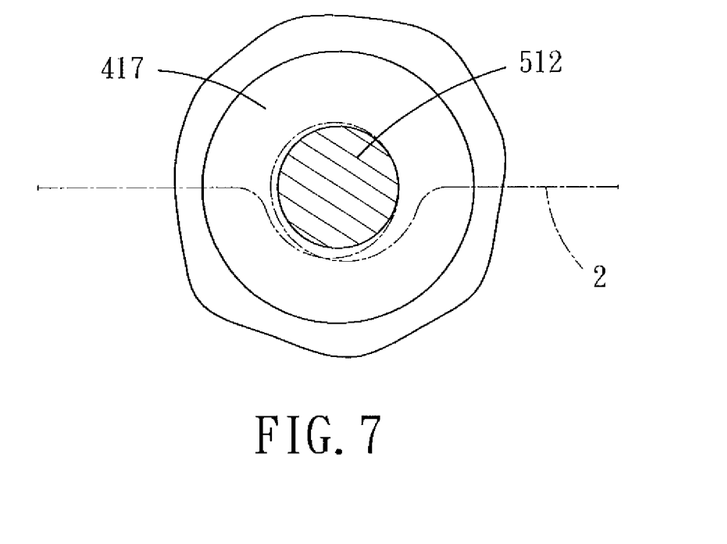
FIG. 7 is yet another sectional view of the first preferred embodiment, illustrating that a segment of a dental floss roll is wound on the adjusting screw.

In this embodiment, the floss holder 4 further includes a clamp unit 410 that is disposed in the guiding channel 45 between the sleeve portion 41 and the screw nut 414, and that has a first clamp plate 416 disposed to be distal from the screw nut 414, and a second clamp plate 417 disposed adjacent to the screw nut 414. Thus, a concealed floss segment of the dental floss roll 2 can be pulled out from the receiving space 36 to pass through the dental floss outlet 352 and the dental floss inlet 401, to be wound on the shank portion 512 of the adjusting screw 51, and to be clamped by the first and second clamp plates 416, 417 of the clamp unit 410. Referring to FIG. 7, the concealed floss segment of the dental floss roll 2 is preferably wound on the shank portion 512 for one and a half turn to provide effective clamping.

As shown in FIG. 3, the bow portion 42 together with the adjusting screw 51, the adjusting cap 52 and the connecting portion 33 of the main body 3, define cooperatively a first opening 6. The bow portion 42 of the floss holder 4 is provided with an open end 421 that is formed with an opening to spatially communicate the guiding channel 45 with external environment. The adjusting cap 52 cooperates with the adjusting screw 51 to form a securing end 56 that is spaced apart from the open end 421. A to-be-used segment 21 of the dental floss roll 2, which is connected to the concealed floss segment, is then extendible through the opening of the open end 421 via the guiding channel 45 so as to be secured at the securing end 56 (i.e., being wound on the shank portion 512 for preferably one or two turns in a clockwise direction and being clamped between the abutting section 5231 of the second surrounding portion 523 and the head portion 511 of the adjusting screw 51). The handle portion 31, the extending portion 32, and the connecting portion 33 cooperate to define a second opening 37 to be spanned by an extending segment 22 of the dental floss roll 2 extending from the securing end 56. In this embodiment, the first body piece 34 is formed with a receiving groove 351 at the handle portion 31 of the main body 3 (see FIG. 3). Moreover, the main body 3 preferably includes a cutting component 38 disposed in the receiving groove 351 and configured for cutting off an unwanted segment of the dental floss roll 2. That is, a used segment of the dental floss roll 2 can be pulled to pass the securing end 56 and the second opening 37 to the receiving groove 351 for being cut by the cutting component 38. In this embodiment, the first clamp plate 416, the second clamp plate 417, and the second surrounding portion 523 of the adjusting cap 52 are made of silicone for enhancing grip to the segments of the dental floss roll 2. However, the composition thereof should not be limited to the disclosure of the present invention.

It is worth noting that the base segment 411 of the sleeve portion 41 cooperates with the screw nut 414, which engages the adjusting screw 51, to clamp the first and second clamp plates 416, 417 of the clamp unit 410. Therefore, by rotating the adjusting cap 52 to drive the adjusting screw 51 to rotate, the screw nut 414 can be moved toward or away from the second clamp plate 417 via the external screw thread 514, so as to be able to adjust the tightness of the first and second clamp plates 416, 417. Further, since the adjusting unit 5 rotates simultaneously while rotating the bow portion 42, the tautness of the to-be-used segment 21 of the dental floss roll 2 may not be affected.

While assembling the interdental cleaning device of the present invention, friction will be generated between the sleeve portion 41 and the first washer 54 and between the sleeve portion 41 and the second washer 55 owing to the movement of the screw nut 414 on the adjusting screw 51. Thus, when a user pulls the bow portion 42 to drive the sleeve portion 41 to rotate, a desired position of the bow portion 42 can be retained due to the friction acting on the sleeve portion 41.

Figure 8:
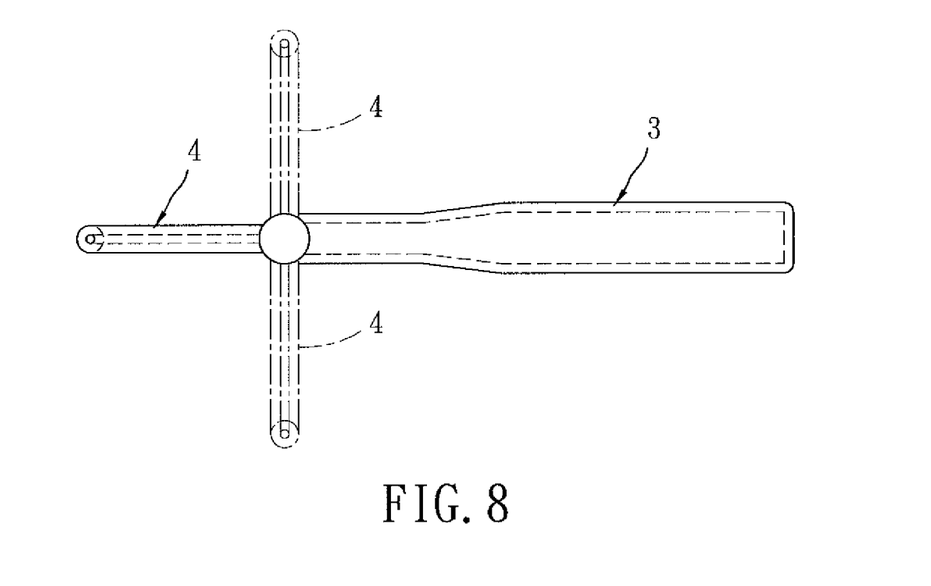
FIG. 8 is a schematic top view of the first preferred embodiment, illustrating that a floss holder is pivotally connected to a main body.
Figure 9:
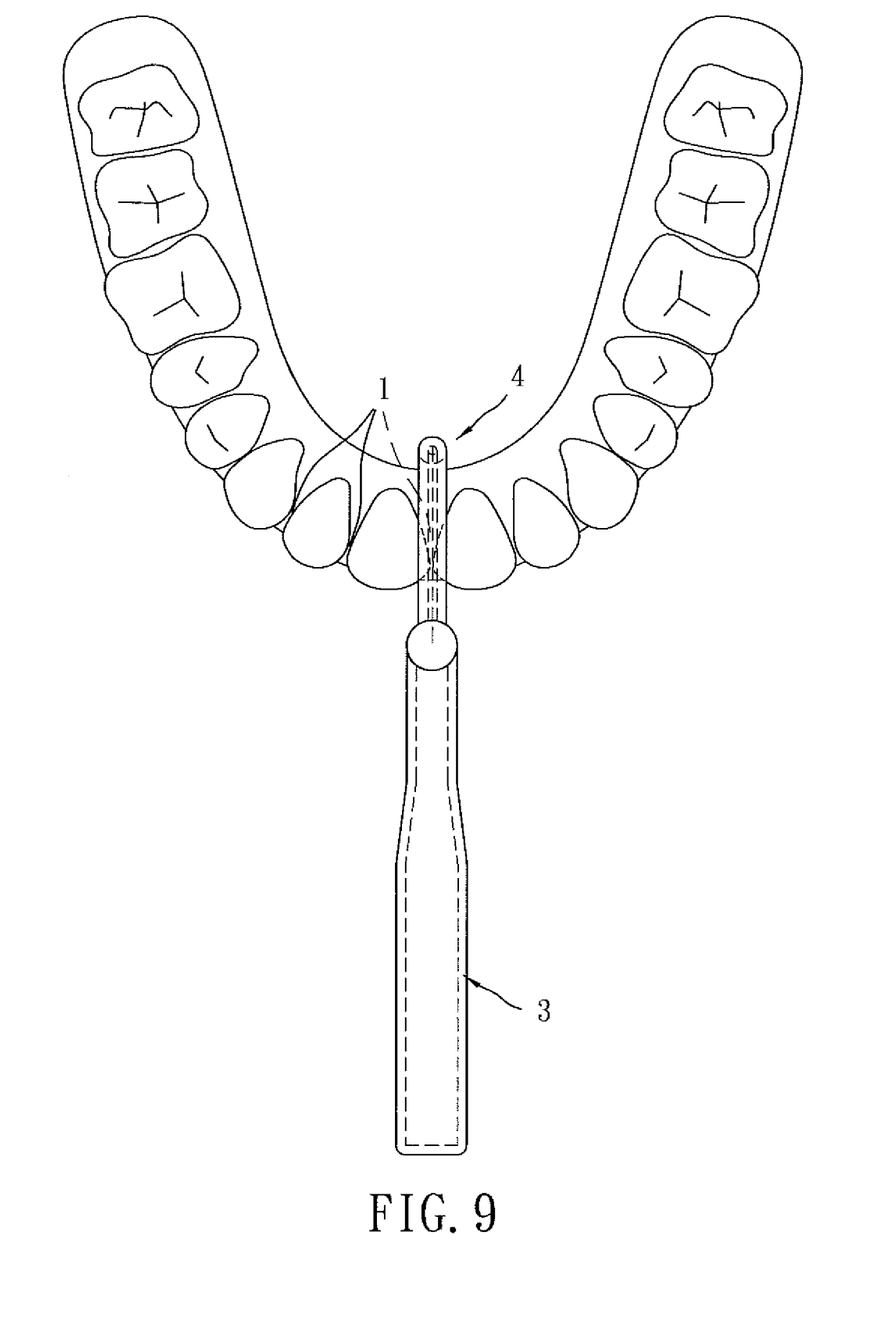
FIG. 9 is a schematic top view of the first preferred embodiment, illustrating that the interdental cleaning device is used to clean an interdental space located in the front of a user's mouth.
Figure 10:
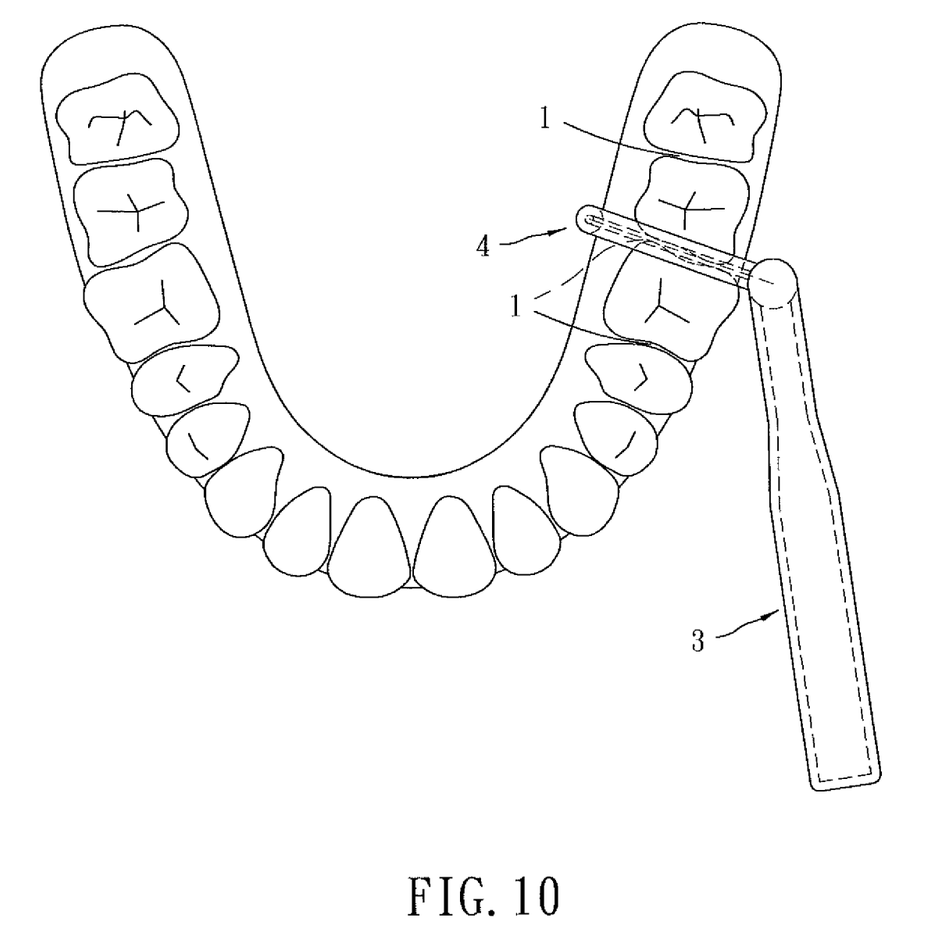
FIG. 10 is a schematic top view of the first preferred embodiment, illustrating that the interdental cleaning device is used to clean an interdental space located in the rear of the user's mouth.

Referring back to FIG. 3 and further referring to FIGS. 8, 9 and 10, when the user intends to use the interdental cleaning device of the present invention to clean the interdental space 1 thereof, the angle between the main body 3 and the floss holder 4 can be adjusted so as to easily place the to-be-used segment 21 into various interdental spaces 1. For example, if the user wants to clean up the interdental space 1 located in the front of his/her mouth (e.g., between incisors), there is no need to adjust the angle of the floss holder 4 relative to the main body 3. As shown in FIG. 10, if the user wants to clean up the interdental space 1 located in the rear of his/her mouth (e.g., between molars), the user may pull to rotate the floss holder 4 to a proper angle, which can be retained due to the friction between the sleeve portion 41 and the first and second washers 54, 55, relative to the main body 3 using his/her hands.

It is also worth noting that the user can adjust the tightness of the to-be-used segment 21 of the dental floss roll 2 by rotating the adjusting cap 52 based on his/her preference or demand.

Figure 11:
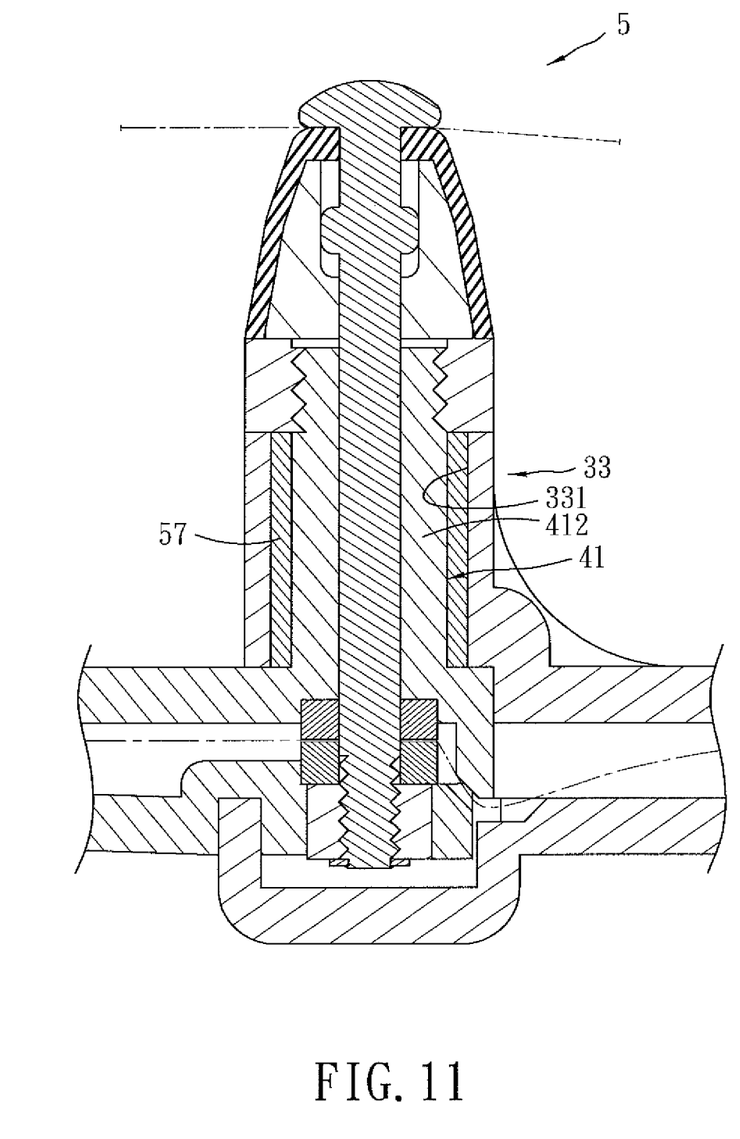
FIG. 11 is a fragmentary sectional view to illustrate a modification of the first preferred embodiment, which includes a bushing.

Referring to FIG. 11, another implementation of the adjusting unit 5 is shown, which omits the first and second washers 54, 55, and which includes a bushing 57 that is sleeved on the post segment 412 of the sleeve portion 41 in the through hole 331 of the connecting portion 33. The friction to retain the bow portion 42 at a desired position is then generated between the bushing 57 and each of the post segment 412 and the connecting portion 33.

Figure 12:
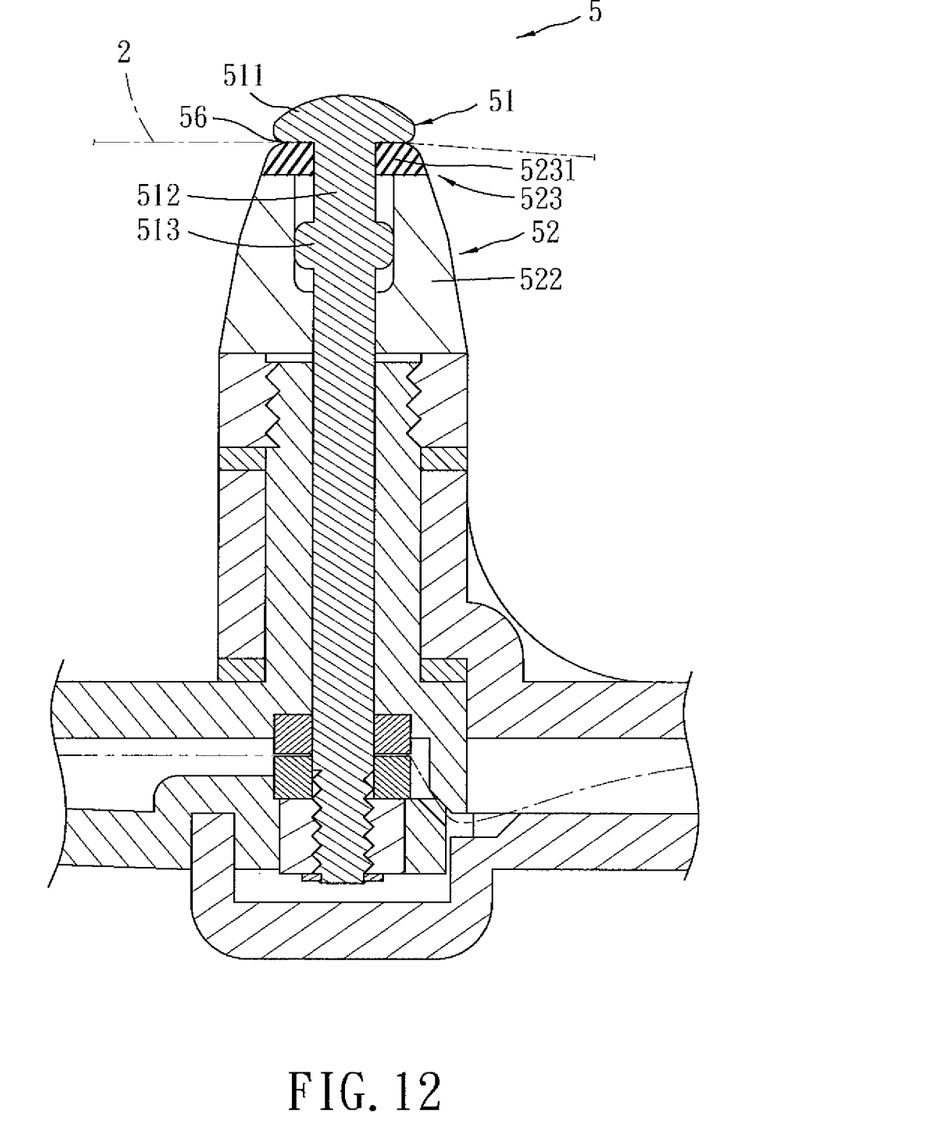
FIG. 12 is a fragmentary sectional view of the first preferred embodiment, illustrating a variation of the adjusting cap.

Referring to FIG. 12, another implementation of the adjusting cap 52 is shown, which omits the surrounding section 5232 of the second surrounding portion 523. Hence, the user may make direct contact with the first surrounding portion 523 while rotating the adjusting cap 52.

Figure 13:
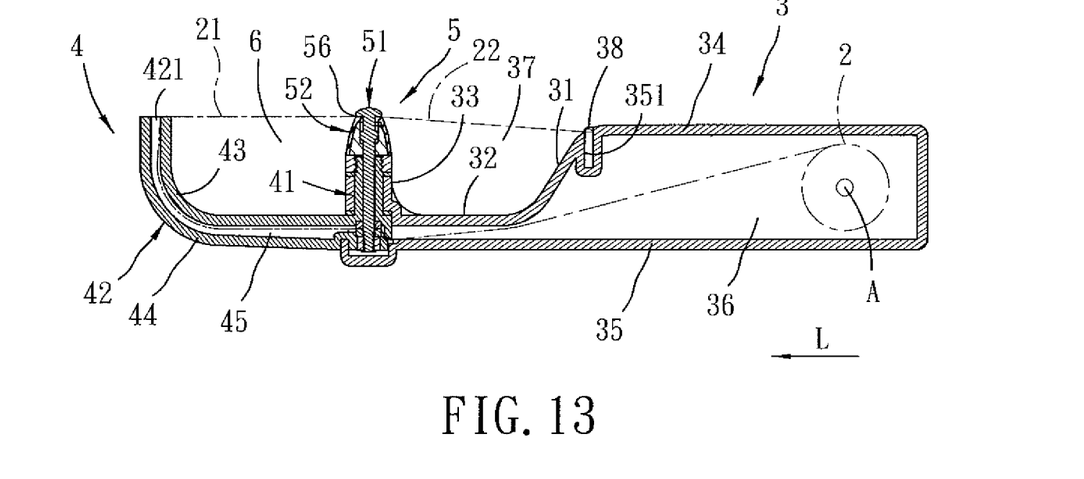
FIG. 13 is a sectional view of another modification of the first preferred embodiment, illustrating that the dental floss roll has a roll axis perpendicular to a longitudinal direction of the main body.
Figure 14:
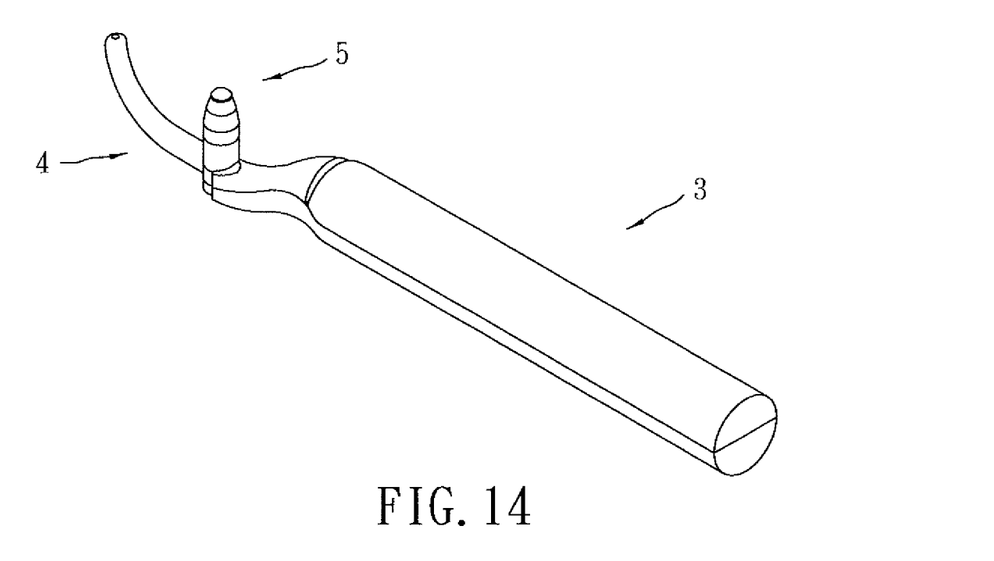
FIG. 14 is a perspective view of a second preferred embodiment of the interdental cleaning device according to the present invention.
Figure 15:
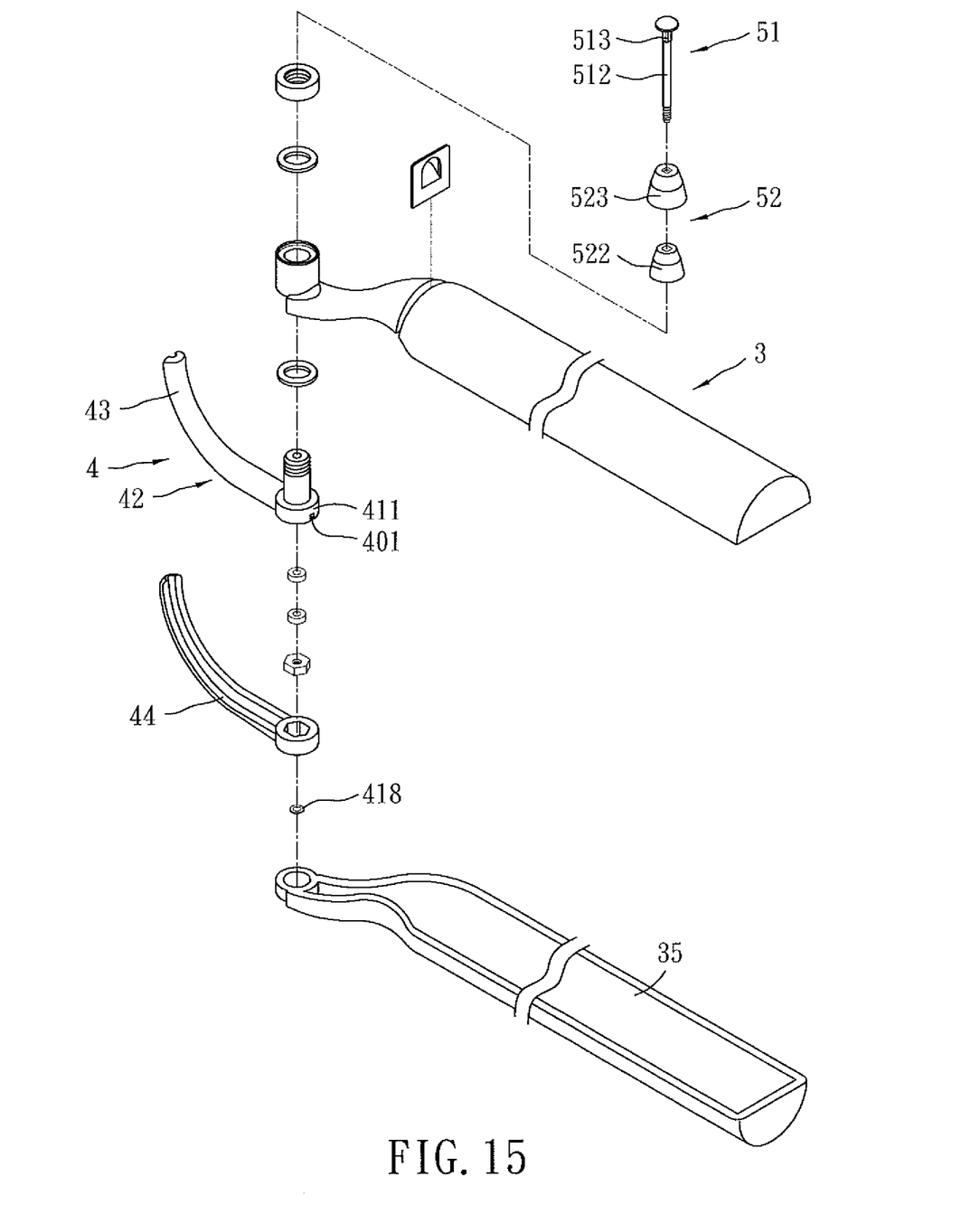
FIG. 15 is an exploded perspective view of the second preferred embodiment.

Referring to FIG. 13, another implementation of the dental floss roll 2 is shown to have the roll axis (A) perpendicular to the longitudinal direction (L) of the main body 3.

Referring to FIGS. 14 to 17, the second preferred embodiment of the interdental cleaning device according to the present invention is shown to be similar to that of the first preferred embodiment. The differences therebetween reside in configurations of the adjusting screw 51 and the adjusting cap 52, and how the receiving space 36 of the main body 3 spatially communicates with the guiding channel 45 of the floss holder 4.

Figure 17:
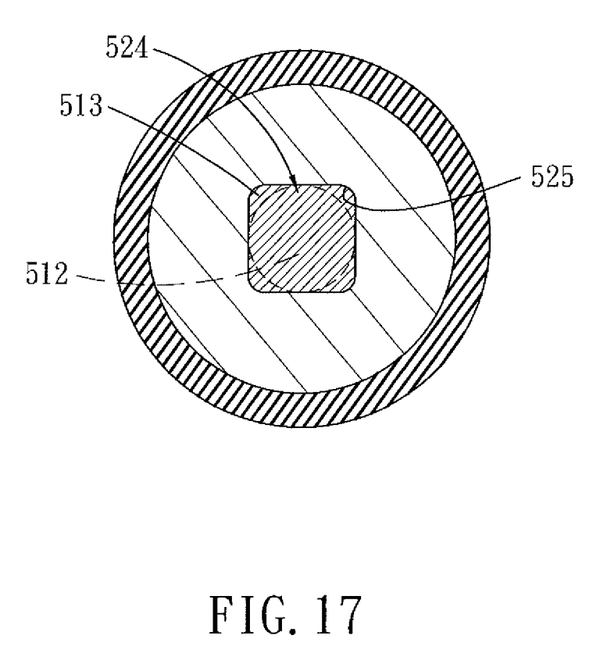
FIG. 17 is a sectional view illustrating the adjusting cap and the adjusting screw of the second preferred embodiment.

As shown in FIG. 17, the through bore 524 has a non-circular engaging section 525, and the adjusting screw 51 has a linking portion 513 extending through the non-circular engaging section 525 and having a non-circular cross-section corresponding to the non-circular engaging section 525. In this embodiment, the linking portion 513 has a quadrilateral cross-section corresponding to the non-circular engaging section 525, thereby coupling co-rotatably the adjusting screw 51 and the adjusting cap 52.

Figure 16:
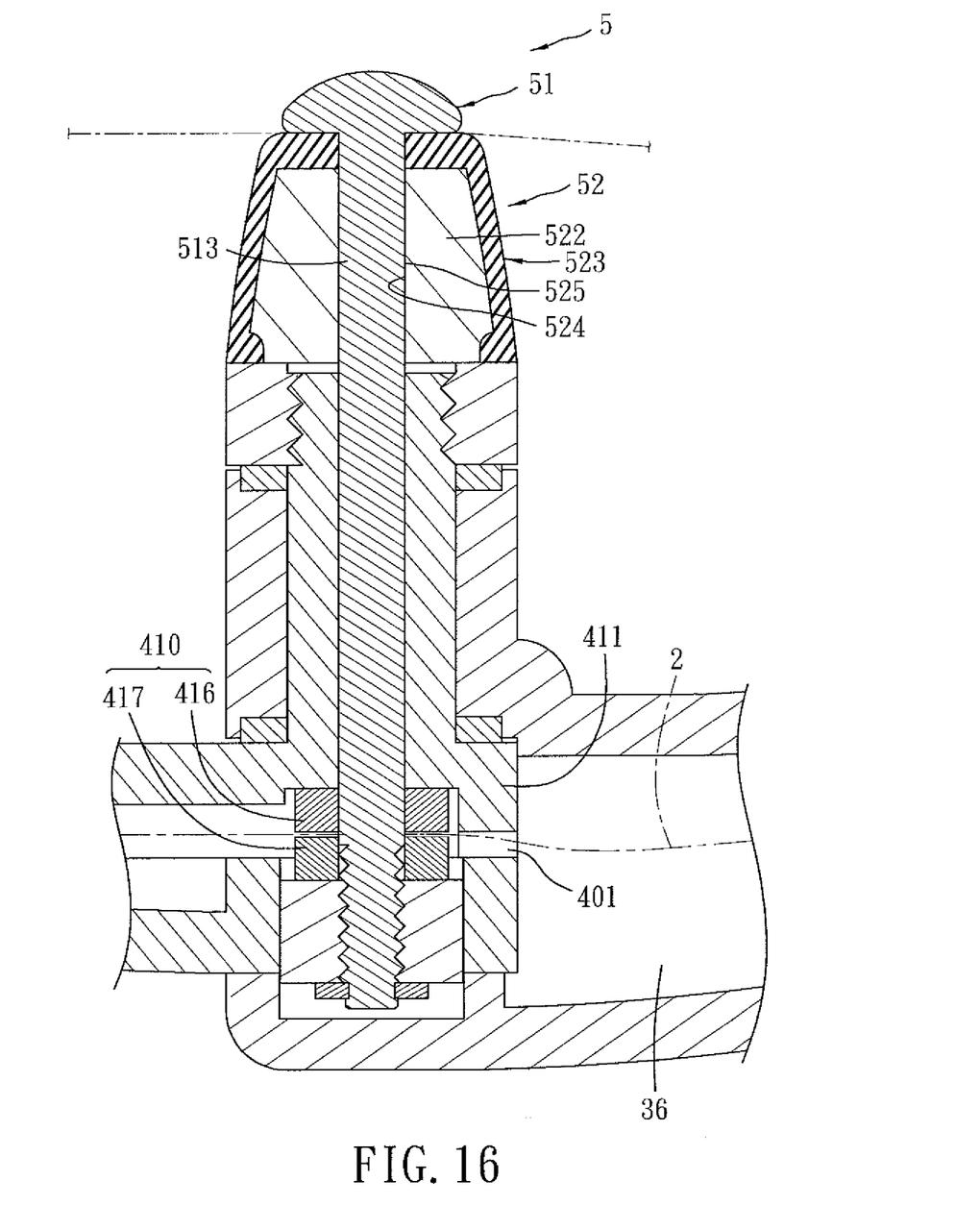
FIG. 16 is a fragmentary sectional view of the second preferred embodiment.

As shown in FIG. 16, in addition, the dental floss outlet 352 of the second body piece 35 (see FIG. 1) is omitted in this embodiment, and the dental floss inlet 401 is formed at the base segment 411 of the sleeve portion 41 which is proximate to the receiving space 36, thereby allowing the concealed floss segment to extend horizontally from the receiving space 36 into the guiding channel 45 via the dental floss inlet 401. Such configuration may prevent the concealed floss segment of the dental floss roll 2 from being stuck at the dental floss inlet 401 and provide relatively smooth introduction of the concealed floss segment in comparison to the first preferred embodiment (see FIG. 4) while rotating the floss holder 4.

To sum up, the bow portion 42 of the interdental cleaning device according to the present invention can be pulled to rotate relative to the connecting portion 33 and can be retained at a desired position due to the friction generated between the sleeve portion 41 and the connecting portion 33. Moreover, the tightness of the to-be-used segment 21 of the dental floss roll 2 is adjustable by rotating the adjusting cap 52, which alters the tightness of the clamp unit 410 via the movement of the screw nut 414 relative to the adjusting screw 51.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An interdental cleaning device adapted for use with a dental floss roll, said interdental cleaning device comprising:
   a main body defining a receiving space configured to receive the dental floss roll; and
   a floss holder pivotally connected to said main body and defining a guiding channel that is in spatial communication with said receiving space, said floss holder having a securing end, and an open end that is spaced apart from said securing end and that is formed with an opening to spatially communicate said guiding channel with external environment;

whereby a to-be-used segment of the dental floss roll is extendible through said opening of said open end via said guiding channel so as to be secured at said securing end of said floss holder;

wherein said main body has a connecting portion, said floss holder including a bow portion that is connected to and rotatable relative to said connecting portion of said main body, and that is provided with said open end;

wherein said connecting portion of said main body is formed with a through hole, said floss holder further including a sleeve portion that is connected to said bow portion and that extends into said through hole, and an adjusting unit including an adjusting screw that extends into and is retained at said sleeve portion, and an adjusting cap that is coupled co-rotatably to said adjusting screw and that cooperates with said adjusting screw to form said securing end of said floss holder;

wherein said adjusting cap is formed with a non-circular through bore, and said adjusting screw has a portion extending through said non-circular through bore and having a non-circular cross-section corresponding to said non-circular through bore, thereby coupling co-rotatably said adjusting cap and said adjusting screw.

2. The interdental cleaning device as claimed in claim 1, wherein said adjusting unit further includes a bushing sleeved on said sleeve portion in said through hole of said connecting portion of said main body.

3. An interdental cleaning device adapted for use with a dental floss roll, said interdental cleaning device comprising:
   a main body defining a receiving space configured to receive the dental floss roll; and
   a floss holder pivotally connected to said main body and defining a guiding channel that is in spatial communication with said receiving space, said floss holder having a securing end, and an open end that is spaced apart from said securing end and that is formed with an opening to spatially communicate said guiding channel with external environment;
   whereby a to-be-used segment of the dental floss roll is extendible through said opening of said open end via said guiding channel so as to be secured at said securing end of said floss holder;
   wherein said main body has a connecting portion, said floss holder including a bow portion that is connected to and rotatable relative to said connecting portion of said main body, and that is provided with said open end;
   wherein said connecting portion of said main body is formed with a through hole, said floss holder further including a sleeve portion that is connected to said bow portion and that extends into said through hole, and an adjusting unit including an adjusting screw that extends into and is retained at said sleeve portion, and an adjusting cap that is coupled co-rotatably to said adjusting screw and that cooperates with said adjusting screw to form said securing end of said floss holder;
   wherein said adjusting cap is formed with a through bore and an engaging trench extending radially outward from and in spatial communication with said through bore;
   wherein said adjusting screw has a head portion disposed to abut against said adjusting cap, a shank portion that is connected to said head portion and that extends through said through bore of said adjusting cap, and a linking portion that protrudes from said shank portion and that engages said engaging trench of said adjusting cap.

4. The interdental cleaning device as claimed in claim 3, wherein said adjusting cap is formed with two of said engaging trenches, and said adjusting screw has two of said linking portions engaging respectively said engaging trenches.

5. The interdental cleaning device as claimed in claim 3, wherein said adjusting cap has a first surrounding portion formed with said engaging trench, and a second surrounding portion disposed on said first surrounding portion and disposed to cooperate with said head portion of said adjusting screw to secure the segment of the dental floss roll therebetween, said through bore being formed through said first surrounding portion and said second surrounding portion.

6. The interdental cleaning device as claimed in claim 5, wherein said second surrounding portion has an abutting section that is disposed to abut against said head portion of said adjusting screw, and a surrounding section that is connected to said abutting section and that cooperates with said abutting section to cover said first surrounding portion.

7. The interdental cleaning device as claimed in claim 3, wherein said shank portion of said adjusting screw has a distal end that is distal from said head portion and that is formed with an external screw thread, and said floss holder further includes:
   a screw nut disposed in said guiding channel and engaging said external screw thread of said adjusting screw so as to retain said adjusting screw at said sleeve portion and so as to pivotally connect said sleeve portion to said connecting portion of said main body; and
   a clamp unit disposed in said guiding channel between said sleeve portion and said screw nut and configured to clamp a concealed segment of the dental floss roll that is connected to the to-be-used segment.

8. The interdental cleaning device as claimed in claim 7, wherein said clamp unit includes two clamp plates.

9. The interdental cleaning device as claimed in claim 3, wherein said adjusting unit further includes a bushing sleeved on said sleeve portion in said through hole of said connecting portion of said main body.

10. An interdental cleaning device adapted for use with a dental floss roll, said interdental cleaning device comprising:
    a main body defining a receiving space configured to receive the dental floss roll; and
    a floss holder pivotally connected to said main body and defining a guiding channel that is in spatial communication with said receiving space, said floss holder having a securing end, and an open end that is spaced apart from said securing end and that is formed with an opening to spatially communicate said guiding channel with external environment;
    whereby a to-be-used segment of the dental floss roll is extendible through said opening of said open end via said guiding channel so as to be secured at said securing end of said floss holder;
    wherein said main body has a connecting portion, said floss holder including a bow portion that is connected to and rotatable relative to said connecting portion of said main body, and that is provided with said open end;
    wherein said connecting portion of said main body is formed with a through hole, said floss holder further including a sleeve portion that is connected to said bow portion and that extends into said through hole, and an adjusting unit including an adjusting screw that extends into and is retained at said sleeve portion, and an adjusting cap that is coupled co-rotatably to said adjusting screw and that cooperates with said adjusting screw to form said securing end of said floss holder;
    wherein said sleeve portion of said floss holder has an exposed segment that is exposed from said through hole of said connecting portion and that is formed with an external screw thread, said adjusting unit further including an adjusting nut that is disposed between said connecting portion and said adjusting cap and that engages said external screw thread on said exposed segment of said sleeve portion.

11. The interdental cleaning device as claimed in claim 10, wherein said sleeve portion of said floss holder further has a base segment and a post segment that extends from said base segment into said through hole of said connecting portion and that has a diameter less than that of said base segment, said exposed segment extending from said post segment, said adjusting unit further including a first washer sleeved on said post segment and disposed between said connecting portion and said base segment.

12. The interdental cleaning device as claimed in claim 11, wherein said adjusting unit further includes a second washer sleeved on said post segment and disposed between said adjusting nut and said connecting portion.

* * * * *